United States Patent
Cai et al.

(10) Patent No.: US 11,922,479 B2
(45) Date of Patent: Mar. 5, 2024

(54) ARTIFICIAL INTELLIGENCE ASSISTED TECHNOLOGY FOR GROCERY RECOMMENDATION AND NUTRIENT OPTIMIZATION

(71) Applicant: Lili Xu Cai, Silver Spring, MD (US)

(72) Inventors: Lili Xu Cai, Silver Spring, MD (US); Emily Edwards Kearney, Brooklyn, NY (US); Antoine Petit, New Rochelle, NY (US); Valentin Alexander Skoutnev, Princeton, NJ (US)

(73) Assignee: Lili Xu Cai, Silver Spring, MD (US)

( * ) Notice: Subject to any disclaimer, the term of this patent is extended or adjusted under 35 U.S.C. 154(b) by 290 days.

(21) Appl. No.: 17/157,649

(22) Filed: Jan. 25, 2021

(65) Prior Publication Data

US 2022/0237681 A1 Jul. 28, 2022

(51) Int. Cl.
*G06Q 30/00* (2023.01)
*G06N 5/02* (2023.01)
(Continued)

(52) U.S. Cl.
CPC .......... *G06Q 30/0631* (2013.01); *G06N 5/02* (2013.01); *G06N 5/04* (2013.01); *G06N 20/00* (2019.01); *G16H 20/60* (2018.01)

(58) Field of Classification Search
CPC .... G06Q 30/06–08; G16H 20/60; G06N 5/02; G06N 5/04
See application file for complete search history.

(56) References Cited

U.S. PATENT DOCUMENTS 8,260,787 B2 9/2012 Lam et al.
8,647,121 B1 2/2014 Witlin et al.
(Continued)

OTHER PUBLICATIONS

Cai, Lili "Nutricart—You tube", retrieved from the internet on Jan. 25, 2021 at <<https://www.youtube.com/watch?v=TqTF6U1C2a8>>, 6 pages.
(Continued)

*Primary Examiner* — Ethan D Civan
(74) *Attorney, Agent, or Firm* — Hamre, Schumann, Mueller & Larson, P.C.

(57) ABSTRACT

Artificial intelligence (AI) assisted technology for grocery recommendations and nutrient optimization includes an intuitive application (app) that can use AI to improve grocery recommendations during grocery shopping to optimize nutrition and encourage users to purchase foods that can help the user receive more complete nutrition. Automatically capturing nutritional information while grocery shopping can assist users seeking to improve their health because it operates while users are performing their grocery shopping, when users have the best opportunity to shape the foods that will be available to them to consume. Nutritional optimization while grocery shopping can improve the use of resources including time and money (due to the cost of food) because it can provide suggestions to address nutritional opportunities that represent nutritional surpluses and nutritional opportunities that represent nutritional deficits. Nutritional optimization while grocery shopping can recommend complementary food items to improve nutritional deficits while minimizing nutritional surplus.

20 Claims, 6 Drawing Sheets

(51) Int. Cl.
    *G06N 5/04*         (2023.01)
    *G06N 20/00*       (2019.01)
    *G06Q 30/0601*   (2023.01)
    *G16H 20/60*      (2018.01)

(56) References Cited

U.S. PATENT DOCUMENTS

| | | | |
|---|---|---|---|
| 10,719,869 B1 | 7/2020 | Dillon | |
| 2013/0196297 A1* | 8/2013 | Anwar | G16H 40/67 434/236 |
| 2016/0278411 A1* | 9/2016 | Wayman | G16H 20/60 |

OTHER PUBLICATIONS

Kendall, Marty, "Nutrient-dense foods on a budget . . . optimised for YOUR goal", retrieved from the internet on Jan. 25, 2021 at <<https://optimisingnutrition.com/nutrient-dense-foods-on-a-budget-optimised-for-fat-different-goals/>>, 11 pages.

"MyFitnessPal", retrieved from the interent on Jan. 25, 2021 at <<https://www.myfitnesspal.com>>, 5 pages.

"Nutricart", retrieved from the internet on Jan. 25, 2021 at <<http://datanalytics.me:8501>>, 1 page.

Nutrient Optimiser, retrieved from the internet on Jan. 25, 2021 at <<https://nutrientoptimiser.com>>, 5 pages.

"Optimising Nutrition" retrieved from the internet on Jan. 25, 2021 at <<https://optimizingnutrition.com>>, 8 pages.

Sarkar, Tirthajyoti, "Linear programming and discrete optimization with Python using PuLP", retrieved from the internet on Jan. 25, 2021 at <<https://towardsdatascience.com/linear-programming-and-discrete-optimization-with-python-using-pulp-449f3c5f6e99>>, 12 pages.

"Shopwell", retrieved from the internet on Jan. 25, 2021 at <<https://www.innit.com/shopwell/>>, 15 pages.

Van Dooren, Corne, "A Review of the Use of Linear Programming to Optimize Diets, Nutritiously, Economically and Environmentally", retrieved from the internet on Jan. 25, 2021 at <<https://www.ncbi.nlm.nih.gov/pmc/articles/PMC6021504/>>, 20 pages.

"Wholesome", retrieved from the internet on Jan. 25, 2021 at <<www.wholesomeapp.com >>, 7 pages.

Zhang, Heng-Ru et al., "Three-way recommender systems based on random forests", Knowledge-Based Systems 91 (2016), retrieved from the internet on Jan. 25, 2021, 275-286.

\* cited by examiner

400(1)

SHOPPING CART 402

Apples, chicken breast, lettuce, broccoli, brown rice, steak, carrots, cheddar cheese, almond milk RECOMMENDED ITEMS: 404
1 Salt free seasoning
2 Organic young jackfruit
3 Potatoes

| | Br Rice | Van Alm Milk | Broccoli | Steak Str | Apples | Carrots | Ched Chs | Lettuce | Chkn Brst | SF Season | Jackfruit | Potatoes |
|---|---|---|---|---|---|---|---|---|---|---|---|---|
| Calories | 19.8 | 1.8 | 1.9 | 9.7 | 2.8 | 2 | 23.8 | 1 | 5.9 | 2 | 2.5 | 12 |
| Total Fat | 4.9 | 1.4 | 0 | 7.3 | 0 | 0 | 49.5 | 0 | 1.2 | 1 | 0 | 0 |
| Sat Fat | 0 | 0 | 0 | 3.2 | 0 | 0 | 119 | 0 | 0 | 0 | 0 | 0 |
| Trans Fat | 0 | 0 | 0 | 0 | 0 | 0 | 0 | 0 | 0 | 0 | 0 | 0 |
| Cholesterol | 0 | 0 | 0 | 10 | 0 | 0 | 39.6 | 0 | 16.6 | 0 | 0 | 0 |
| Sodium | 0 | 2.9 | 1.1 | 24.4 | 0 | 2 | 32.8 | 0.28 | 2.2 | 0 | 0.5 | 0 |
| Carbohydrate | 29.7 | 2.2 | 1.8 | 0 | 5.5 | 2 | 1.3 | 1.3 | 1.3 | 0 | 3.9 | 9 |
| Fiber | 18 | 1.5 | 9.2 | 0 | 12.3 | 7 | 0 | 0 | 0 | 4 | 30 | 8 |
| Sugar | 0 | 10 | 4.3 | 0 | 19.2 | 0 | 0 | 2.5 | 2.7 | 0 | 4.9 | 0 |
| Protein | 15 | 0.9 | 2.5 | 58.8 | 0 | 1 | 54.3 | 2.5 | 40.7 | 0 | 4.8 | 3 |
| Vitamin D | 0 | 25 | 0 | 0 | 0 | 0 | 0 | 0 | 0 | 0 | 0 | 0 |
| Calcium | 1 | 18.8 | 2.4 | 2 | 0 | 2 | 2 | 2.4 | 0 | 2 | 3 | 2 |
| Iron | 13.2 | 0.8 | 0 | 17.6 | 1.2 | 1 | 55.4 | 4.7 | 3.5 | 10 | 7 | 6 |
| Potassium | 5.3 | 1.5 | 0 | 2.8 | 2.3 | 0 | 1 | 0 | 0 | 2.2 | 22 | 20 |
| Vitamin A | 0 | 29.7 | 16.8 | 0 | 9.2 | 204 | 24.1 | 2.1 | 2 | 0 | 2 | 0 |
| Vitamin C | 0 | 0 | 47 | 0 | 4.1 | 6 | 0 | 0 | 2.8 | 0 | 23 | 45 |

FIG. 4B

ARTIFICIAL INTELLIGENCE ASSISTED TECHNOLOGY FOR GROCERY RECOMMENDATION AND NUTRIENT OPTIMIZATION

BACKGROUND

Historically, nutrition tracking required users to manually record the food they consumed. Users generally did this by writing consumed items in a notepad and referring to general food information to determine the corresponding nutrient content. This process required time and continued effort from the user, which could lead to omissions or abandoning the practice. To save time, users sometimes limit themselves to tracking only select nutrients such as fat or calories and therefore would not have a full understanding of their food's comprehensive nutrient content. Additionally, manual tracking required users to do their own calculations of total nutrient intake, which raised the risk of errors. Users also had to independently research and seek foods that optimized their nutrient intake, which could yield suboptimal results due a user's limited exposure to and knowledge of all possible foods and their nutrient contents.

Traditional app-based nutrition tracking has been adopted by some users. Traditional app-based nutrition tracking allowed users to enter what they were eating into a computer program or a phone app, rather than needing to carry a notepad, and alleviated the need to look up some corresponding nutritional information. In the last several years, app-based nutrition tracking evolved to incorporate rich nutritional information into apps available for various devices, i.e., FITBIT, MYFITNESSPAL. Some of these newer conventional apps provided more nutrition information than Calories and fat tracking, and at least one provided a static list of foods high in certain nutrients, i.e., SAMSUNG HEALTH. At least one conventional approach (SHOPWELL) recommends alternatives specific to a food product category that might be beneficial to the user: e.g., low sugar yogurt instead of high sugar yogurt. Some of these newer conventional apps provided different interfaces for users to record their consumption like the ability to scan bar codes from packaged foods and the ability to search previous records. Nevertheless, both traditional and newer conventional app-based nutrition tracking still relied on user effort, causing the process of tracking nutrition to still be time consuming and tedious for users, and prone to omissions. Additionally, recommended items were not tailored to optimize overall nutrition of an individual's food consumption behavior. Moreover, these conventional app-based methods requiring that the user enter their consumption, was and always will be limited to the food available to the user at the time of their meal or snack.

Recently online grocery shopping has been adopted by many people. Online grocery shopping makes it easy for users to purchase grocery items for pick up or delivery. However, since the user doing the online shopping does not go into a physical store to pick out their groceries, some users are more likely to forget items or select items that do not meet their nutritional needs.

Whether offline or online, users seeking to improve their nutrition are limited by their subjective knowledge and awareness of food nutrients. Accordingly, there is an opportunity to improve users' nutrition by using artificial intelligence to provide recommendations to optimize nutrients based on items in a user's online grocery cart.

SUMMARY

This disclosure describes systems, methods, and computer-executable instructions on computer-readable media for an artificial intelligence (AI) assisted technology for grocery recommendations and nutrient optimization. This disclosure describes an intuitive application (app) that can use AI to improve grocery recommendations during grocery shopping to optimize nutrition and encourage users to purchase foods that can help the user receive more complete nutrition. Automatically capturing nutritional information while grocery shopping can be important for users seeking to improve their health because it can alleviate the need for users to separately record their consumption whether manually or through a conventional app. Nutritional optimization while grocery shopping as described herein can improve the use of resources including time and food costs because it can provide suggestions to address nutritional opportunities that represent nutritional surpluses and nutritional opportunities that represent nutritional deficits.

This Summary is provided to introduce a selection of concepts in a simplified form that are further described below in the Detailed Description. This Summary is not intended to identify key and/or essential features of the claimed subject matter, nor is it intended to be used as an aid in determining the scope of the claimed subject matter. The term "techniques," for instance, can refer to system(s), method(s), computer-readable instructions, module(s), algorithms, hardware logic, and/or operation(s) as permitted by the context described above and throughout the document.

BRIEF DESCRIPTION OF THE DRAWINGS

The detailed description is described with reference to the accompanying figures. In the figures, the left-most digit(s) of a reference number identifies the figure in which the reference number first appears. The same reference numbers in different figures indicate similar and/or identical items.

FIG. 4B illustrates another part of an example graphical user interface (GUI) associated with AI assisted technology for grocery recommendations and nutrient optimization according to various examples described herein.

DETAILED DESCRIPTION

Overview

Figure 1:
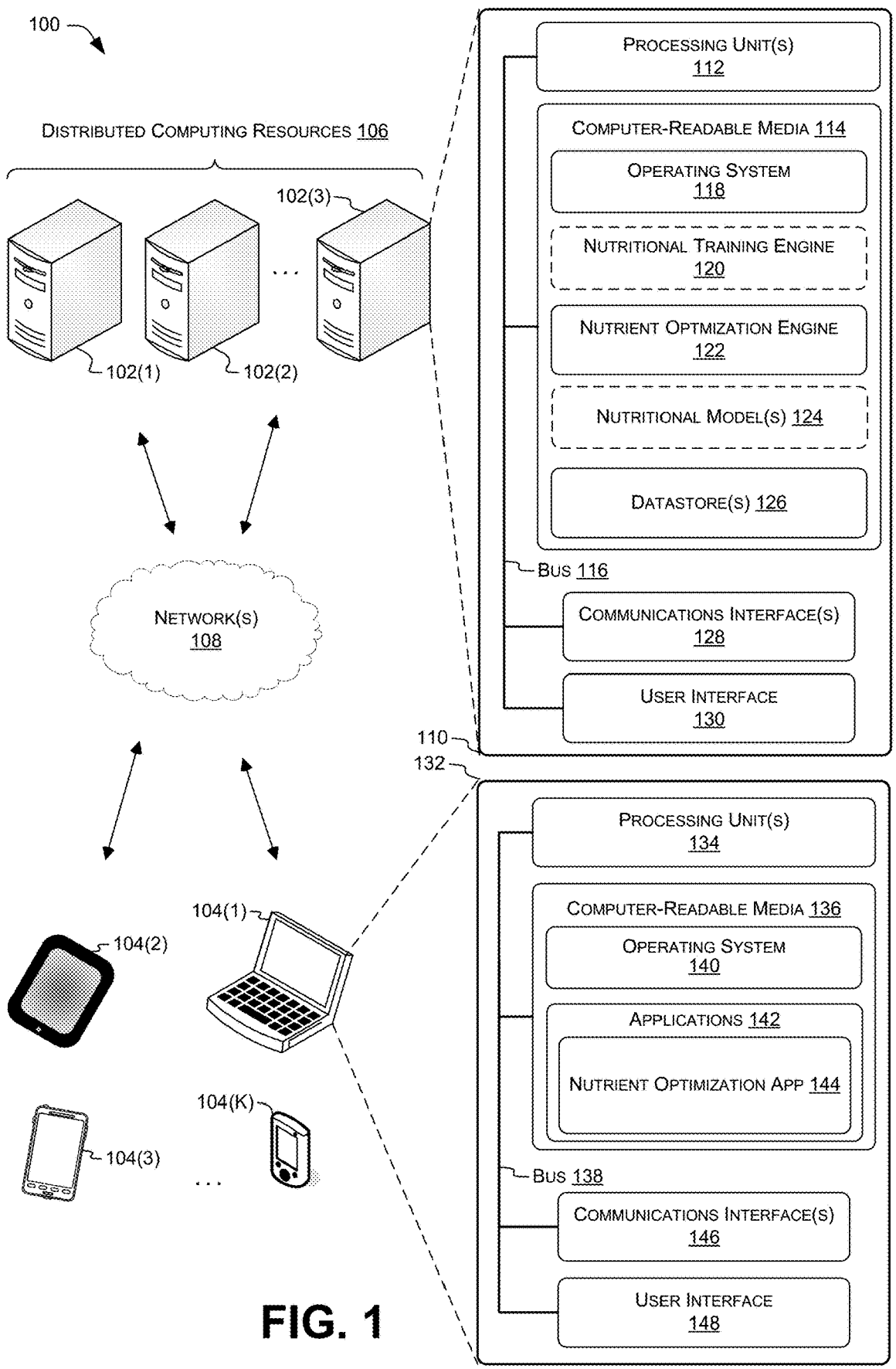
FIG. 1 is a block diagram depicting an example environment for implementing AI assisted technology for grocery recommendations and nutrient optimization as described herein.

The goal of the innovation described herein is to make nutrition information and customized grocery recommendations effortlessly accessible to people. All of the previous nutrition-tracking methods required that users enter their consumption, which requires that the user either stop preparation of their meal or stop the meal itself, activate an application, then enter information about the meal including the ingredients and portion size, or capture information from bar codes on pre-packaged food using cameras. All of the previous nutrition-tracking methods are limited to focusing on the food available to the user at the time of their meal or snack. Meanwhile, online grocery shopping, as has been adopted by many people, is a platform that provides an opportunity to process nutrition information and generate customized recommendations at no effort to the user, which could encourage users to choose foods that can make their nutrition more complete. Examples described herein can leverage and expand on experiences of online grocery shopping, grocery membership clubs that tie purchases to membership accounts, and/or other shopping experiences, such as smart phone scanning functionalities, to make recommendations that can optimize nutrition while relieving people of the need to record consumption and provide more specific nutrient information for nutrition tracking.

In at least one example, an intuitive app can be installed on a device associated with a user as a standalone app, as an app providing an API for one or more other apps, e.g., grocery shopping apps or delivery apps such as INSTACART, POSTMATES, FRESHDIRECT, FOODKICK, PEAPOD, SHIPT, SCHWAN'S, THRIVE MARKET, AMAZON FRESH, etc., or as a browser extension that can activate when the browser navigates to an online grocery portal such as those associated with grocery stores like KROGER, ALDI, SAFEWAY, WALMART, FRED MEYER, PUBLIX, TARGET, COSTCO, etc. other grocery providers such as GOOGLE SHOPPING, SCHWAN'S, AMAZON FRESH, AMAZON, AMAZON PRIME PANTRY, AMAZON PRIME NOW, BOXED, etc. or meal subscription services like HUNGRYROOT, HELLO FRESH, EVERY PLATE, etc. The app can use AI to improve grocery recommendations during grocery shopping to optimize nutrition according to an identified nutritional opportunity. In at least one example, the app can participate in or broker payments associated with grocery shopping including one or more of charging the user a fee to customize grocery recommendations based on dietary preferences and purchase history, charging grocery providers a fee to access the API so their shoppers can have access to recommendations that improve nutrition, charging sponsors a fee to have their product prioritized in recommendations for a specific food category, charging a grocery retailer a percentage of their increased sales revenue due to the app recommendations, etc.

As used herein a nutritional opportunity represents a deficit or a surplus of one or more nutrients such as calcium, cholesterol, carbohydrates, vitamin A, vitamin C, vitamin D, fiber, iron, potassium, protein, saturated fat, sugar, sodium, etc. In examples, a food item can include various nutrients, such as vitamins, minerals, fiber, macronutrients, probiotics, and/or bacteria such as *I. acidophilus*. In at least one example, nutritional opportunity can represent a relative deficit or a relative surplus compared to overall nutrients and/or recommended daily values from nutritional guidelines.

In some examples, nutrients in a food item include one or more vitamins. Examples of vitamins include vitamin A (e.g., retinol, retinal, alpha carotene, beta-carotene, gamma carotene, cryptoxanthin, or any combination thereof), vitamin B (e.g., thiamine, riboflavin, niacin, pantothenic acid, pyridoxine, pyridoxine 5'-phosphate, pyridoxal, pyridoxal 5'-phosphate, pyridoxamine, pyridoxamine 5'-phosphate, 4-pyridoxic acid, pyritinol, biotin, folic acid, cobalamins, or any combination thereof), vitamin C (e.g., L-ascorbic acid), vitamin D (e.g., cholecalciferol, ergocalciferol, 22-dihydroergocalciferol, sitocalciferol, or any combination thereof), vitamin E (e.g., alpha-tocopherol, beta-tocopherol, gamma-tocopherol, delta-tocopherol, tocopheryl acetate, or any combination thereof), vitamin K (e.g., phylloquinone, menaquinone, or a combination thereof), or any combination thereof.

In some examples, nutrients in a food item include one or more minerals. Examples of minerals include calcium (e.g., calcium carbonate, calcium citrate, calcium gluconate, or the like), chromium (e.g., chromium(III) picolinate), copper (e.g., copper gluconate), iodine (e.g., potassium iodate, calcium iodate, or the like), iron (e.g., iron(II) sulfate), magnesium (e.g., magnesium oxide, magnesium citrate, magnesium chloride, or the like), manganese (e.g., manganese gluconate), selenium (e.g., selenomethionine, sodium selenite, sodium selenite, or a combination thereof), sodium (e.g., sodium chloride), potassium (e.g., potassium chloride), zinc (e.g., zinc gluconate, zinc sulfate, zinc acetate, or the like), or a combination thereof.

In various examples, nutrients in a food item includes fiber. Fiber refers to a component of food that is no more than partially broken down in the human digestive tract. Examples of fiber that is water-soluble (also referred to as "soluble fiber") include inulin, wheat dextrin, psyllium, beta-glucans, and guar gum. Examples of fiber that is water-insoluble (also referred to as "insoluble fiber") includes cellulose and lignin.

In some cases, nutrients in a food item include one or more macronutrients (macros). Macronutrients include, for example, carbohydrates, fats, and proteins. As used herein, the term "carbohydrate," and its equivalents, can refer to a saccharide. Examples of carbohydrates include sugars, starches, and cellulose. As used herein, the term "fat" and its equivalents, can refer to an ester of multiple fatty acids, and/or any other lipid. Fats can be saturated fats, unsaturated fats, trans fats, cis fats, or a combination thereof. Cholesterol, corticosteroids, and androgens, estrogens, and progestogens, are examples of lipids. As used herein, the term "protein," and its equivalents, can refer to a chain of multiple amino acids.

Some nutrients are not synthesized in the human body or are synthesized in limited quantities. People may rely on their diets to obtain these nutrients. Fatty acids that cannot be synthesized or have lower than a threshold conversion efficiency in the human body are referred to as "essential fatty acids," and include linoleic acid, alpha-linolenic acid, eicosatetraenoic acid, docosahexaenoic acid, as well as other omega-3 and omega-6 fatty acids. Amino acids that cannot be synthesized or have lower than a threshold conversion efficiency in the human body are referred to as "essential amino acids," and include histidine, isoleucine, leucine, lysine, methionine, phenylalanine, threonine, tryptophan, and valine. Some amino acids with limited synthesis in the human body include conditionally essential amino acids, such as arginine, cysteine, glutamine, glycine, proline, and tyrosine.

In some examples, nutrient opportunity can be determined according to a recorded serving size of a food item and/or daily recommended value of a nutrient. In various examples, the nutritional opportunity can be identified based on food items in the current shopping order or in more than one shopping order associated with the user and/or within a period of time, e.g., from the previous shopping order, within the current shopping order and from the previous shopping order, within shopping orders from today and yesterday, within shopping orders from today and earlier this week, etc., and in a variety of examples, shopping orders from more than one grocery store.

The app can use AI to identify foods that can help the user receive complete nutrition, which the app can present to the user to encourage purchase of the identified foods. Automatically capturing nutritional information while grocery shopping can be important for improving users' health because it can alleviate the need for users to separately record their consumption whether manually or through an app.

In at least one example, the app includes or can access nutritional guidelines, which are publicly available. In some examples, the app can be configured to include or access specialized nutritional guidelines such as vegetarian, vegan, pescatarian, Mediterranean, keto, etc., specialized nutritional guidelines tailored to avoid food allergies, e.g., gluten free, peanut free, dairy free, etc. and/or specialized nutritional guidelines that account for different needs based on age, sex, and/or activity level. For example, specialized nutritional guidelines can account for factors like premenopausal women need more iron than men, adults tend to need fewer calories than teenagers, athletes need more calories and protein than sedentary people, etc. In some examples, the app can access one or more nutritional guidelines, including the specialized nutritional guidelines like the mentioned example guidelines, via the internet and from one or more agencies of the United States and/or other governments, the American Heart Association, and/or other diet and nutrition related sites such as WEIGHT WATCHERS, etc. In examples, operation of the app can include storing a copy of and/or applying one or more nutritional guidelines. In some examples, the user can customize their own nutritional guideline relative to their own nutritional goals.

In at least one example, a system associated with the app includes a food datastore that includes records associated with a plurality of foods items. A food item can include any comestible item including raw food and/or spices, e.g., fruits, vegetables, nuts, grains, legumes, beef, fish, poultry, etc., types and/or varieties of food including granny smith apple, fuji apple, blood orange, mandarin orange, blueberries, strawberries, broccoli florets, bibb lettuce, walnuts, almonds, brown rice, jasmine rice, green lentils, beef steak, beef roast, hamburger 20% fat, hamburger 5% fat, salmon, cod, whole turkey, whole chicken, chicken breast boneless, chicken thigh, potato chips, tortilla chips, spices, and many more. A food item can include any comestible item including cooked food, particular restaurant dishes, and/or pre-packaged food. The records can include nutritional information including nutrients included in the food item such as calcium, vitamin A, vitamin C, vitamin D, fiber, iron, potassium, protein, saturated fat, sodium, etc. portion size, and/or type of preparation, e.g., raw, baked, poached in water, poached in dry white wine, air fried, fried in oil, etc. Food datastore can include default records associated general food terms for which nutritional information is not otherwise provided, e.g., default nutritional information for "apple" based on the most common type of apples that have been purchased, an average of nutritional information based on the types of apples available, etc. In some examples, if the food datastore does not contain nutritional information for a general food item, a system associated with the app can instigate a search for this information and create a record based on the search results and/or, the system can cause a user interface (UI) to request more specificity about the food item, e.g., "what type of apple?" In some instances where the type is not found in the food datastore or via a search, e.g., due to a typographical error, a system associated with the app can use an algorithm like Levenshtein distance or a similar algorithm to identify the closest match or a likely match. In various examples, the food datastore can be organized by food category. In some examples, a food category can be partitioned by name. For example, a general node "apples" could include Gala apples, Honeycrisp apples, Macintosh Apples, etc. In some examples, a food category can be partitioned using unsupervised learning or generative statistical models on nutrient information. For example, a food category partitioned using unsupervised learning can include kale and spinach because both have high values of vitamin K and vitamin A.

In at least one example, a system associated with the app includes a user datastore that includes records of parameters associated with users including one or more of user identifier, device identifier, family size and/or makeup (infants, children, teens, adults), user age or age range, sex, activity level (sedentary, moderately active, active, athlete), specialty diet(s), food purchase history, storage authorization, registration information, customized nutritional guideline, etc. In some examples, a system associated with the app can incorporate the option for a user to report meals and/or food items acquired without activating the app, e.g., one or more of a restaurant meal, a meal at which the user is a guest, food items acquired from a grocery store without interaction with the app, etc.

In some examples, algorithms for AI assisted grocery recommendations as described herein can be performed on a computing device, such as a smart phone, a tablet, a laptop computer, a hybrid computing device, a desktop computer, a server, a supercomputer, etc. having one or more input devices, such as a physical keyboard, a soft keyboard, a touch screen, a touch pad, microphone(s), and/or camera(s).

Various environments, configurations of computing devices, and methods that can enable AI assisted technology for grocery recommendations and nutrient optimization, are described further with reference to FIGS. 1-5. While many examples described herein refer to distributed computing resources and/or consumer electronic devices, other types of electronic devices can implement such examples, e.g., as discussed with reference to FIG. 1.

Illustrative Environment

FIG. 1 shows an example environment 100 in which examples of AI assisted technology for grocery recommendations and nutrient optimization, can operate and/or in which methods of AI assisted technology for grocery recommendations and nutrient optimization such as those described herein can be performed. In the illustrated example, the various devices and/or components illustrated in environment 100 includes various devices and or components. The illustrated environment includes computing device(s) 102(1)-102(N) (individually and/or collectively referred to herein with reference 102), where N is any integer greater than and/or equal to 1, e.g., server(s) and/or desktop computer(s). The illustrated environment includes computing devices 104(1)-104(K) (individually and/or collectively referred to herein with reference 104), where K is any integer greater than and/or equal to 1. In some examples, N=K; in other examples, N>K or N<K e.g., laptop computer(s), tablet computer(s), hybrid computing device(s), and/or smart phones. Computing device(s) 102 and/or 104 can include a diverse variety of device categories, classes, and/or types and are not limited to any of the particular types of devices illustrated.

In the illustrated example, computing device(s) 102(1)-102(N) can be computing nodes of distributed computing resources 106, e.g., in a computing cluster, such as a cloud service such as MICROSOFT AZURE, VMWARE VCLOUD, RACKSPACE, Inc.'s OPENSTACK, AMAZON WEB SERVICES (AWS), IBM SMARTCLOUD, ORACLE CLOUD, etc. In the illustrated example, computing device(s) 104 can include consumer devices and in some instances can operate as clients of distributed computing resources 106 that can submit jobs to distributed computing resources 106 and/or receive job results from distributed computing resources 106. Computing devices 102(1)-102(N) in distributed computing resources 106 can, share resources, balance load, increase performance, and/or provide fail-over support and/or redundancy, etc. Computing devices 104 can additionally or alternatively operate in a cluster and/or grouped configuration via association with one or more user(s).

By way of example and not limitation, computing device(s) 102 can include, but are not limited to, server computers and/or blade servers such as Web servers, map/reduce servers and/or other computation engines, and/or network-attached-storage units (e.g., 102(1)). By way of example and not limitation, computing device(s) 104 can include, but are not limited to, laptop computers (e.g., 104(1)), tablet computers (e.g., 104(2)), tablet hybrid computers 104(3), smartphones (e.g., 104(4)), and/or other telecommunication devices, desktop computers, and/or integrated components for inclusion in computing devices, appliances, and/or other computing device(s) configured to participate in and/or carry out AI assisted grocery recommendations and nutrient optimization as described herein.

In some examples, as indicated, computing device(s), e.g., computing devices 102 and 104, can intercommunicate to participate in and/or carry out AI assisted grocery recommendations and nutrient optimization as described herein. For example, a computing device 104 can be a query and/or data source and computing device 102 can host components of an AI assisted grocery recommendations and nutrient optimization system to store data, provide recommendations, and/or be queried, as described below with reference to, e.g., FIGS. 2-5.

Different devices and/or types of computing devices 102 and 104 can have different needs and/or ways of interacting with distributed computing resources 106. For example, computing devices 104 can interact with distributed computing resources 106 with discrete request/response communications, e.g., for responses and/or updates using an already-trained nutritional model. Additionally and/or alternatively, computing devices 104 can be query sources and/or data sources and can interact with distributed computing resources 106 with discrete and/or ongoing transmissions of data to be used as input to a nutritional model. This can provide improved personalized optimizations by increasing the number or queries and/or amount of data input to the nutritional model.

In some examples, computing devices 102 and/or 104 can communicate with each other and/or with other computing devices via one or more network(s) 108. In some examples, computing devices 102 and 104 can communicate with external devices via network(s) 108. For example, network(s) 108 can include public networks such as the Internet, private networks such as an institutional and/or personal intranet, and/or combination(s) of private and public networks. Private networks can include networks connected to the Internet and/or other public network(s) via network address translation (NAT) devices, firewalls, network intrusion detection systems, and/or other devices that restrict and/or control the types of network packets permitted to flow between the private network and the public network(s).

Network(s) 108 can also include any type of wired and/or wireless network, including but not limited to local area networks (LANs), wide area networks (WANs), satellite networks, cable networks, Wi-Fi networks, WiMAX networks, mobile communications networks (e.g., 3G, 4G, 5G, and so forth), any combination thereof, etc. Network(s) 108 can utilize communications protocols, such as, for example, packet-based and/or datagram-based protocols such as Internet Protocol (IP), Transmission Control Protocol (TCP), User Datagram Protocol (UDP), other types of protocols, and/or combinations thereof. Moreover, network(s) 108 can also include a number of devices that facilitate network communications and/or form a hardware infrastructure for the networks, such as switches, routers, gateways, access points, firewalls, base stations, repeaters, backbone devices, and the like. Network(s) 108 can also include devices that facilitate communications between computing devices 102 and/or 104 using bus protocols of various topologies, e.g., crossbar switches, INFINIBAND switches, FIBRE CHANNEL switches and/or hubs, etc.

In some examples, network(s) 108 can further include devices that enable connection to a wireless network, such as a wireless access point (WAP). Examples support connectivity through WAPs that send and receive data over various electromagnetic frequencies (e.g., radio frequencies), including WAPs that support Institute of Electrical and Electronics Engineers (IEEE) 802.11 standards (e.g., 802.11g, 802.11n, and so forth), and/or one or more other standards, e.g., BLUETOOTH, cellular-telephony standards such as code division multiple access (CDMA), global system for mobile communication (GSM), $3^{rd}$ Generation Partnership Project (3GPP) standards, such as long-term evolution (LTE) and/or new radio (NR), voice over internet protocols (VOIP), worldwide interoperability for microwave access (WiMAX), etc.

Different networks have different characteristics, e.g., bandwidth, latency, accessibility (open, announced but secured, and/or not announced), and/or coverage area. The type of network 108 used for any given connection between, e.g., a computing device 104 and distributed computing resources 106 can be selected based on these characteristics and on the type of interaction.

Still referring to the example of FIG. 1, details of an example computing device 102(3) are illustrated at inset 110. The details of example computing device 102(3) can be representative of others of computing device(s) 102. However, each of the computing device(s) 102 can include additional or alternative hardware and/or software components.

Illustrated computing device 102 can include one or more processing unit(s) 112, e.g., integrated electronic circuit(s) operably connected to one or more computer-readable media 114, e.g., memories, such as via a bus 116. In some examples, a plurality of processing unit(s) 112 can exchange data through an internal interface bus (e.g., PCIe), rather than and/or in addition to network 108. While the processing unit(s) 112 are described as residing on the computing device 102(3), in this example, the processing unit(s) 112 can also reside on different computing device(s) 102 and/or 104 in some examples. In some examples, at least two of the processing unit(s) 112 can reside on different computing device(s) 102 and/or 104. In such examples, multiple processing unit(s) 112 on the same computing device 102 and/or 104 can use a bus 116 of the computing device 102 and/or 104 to exchange data, while processing unit(s) 112 on different computing device(s) 102 and/or 104 can exchange data via network(s) 108.

Processing unit(s) 112 can include one or more microprocessors, single-core processors, multi-core processors, CPUs, GPUs, GPGPUs, and/or hardware logic components configured, e.g., via specialized programming from modules and/or APIs, to perform functions described herein. For example, and without limitation, illustrative types of hardware logic components that can be used in and/or as processing unit(s) 112 include Field-Programmable Gate Arrays (FPGAs), Application-Specific Integrated Circuits (ASICs), Application-Specific Standard Products (ASSPs), System-on-a-Ship systems (SOCs), Complex Programmable Logic Devices (CPLDs), Digital Signal Processors (DSPs), and other types of customizable processors. For example, a processing unit 114 can represent a hybrid device, such as a device from ALTERA and/or XILINX that includes a CPU core embedded in an FPGA fabric. These and/or other hardware logic components can operate independently and/or, in some instances, can be driven by a CPU. In some examples, at least some of computing device(s) 102 and/or 104 can include a plurality of processing unit(s) 112 of multiple types. For example, the processing unit(s) 112 shown in computing device 102(3) can be a combination of one or more CPUs, GPGPUs, FPGAs, etc. Different processing unit(s) 112 can have different execution models, e.g., as is the case for graphics processing units (GPUs) and central processing unit (CPUs).

Computer-readable media described herein, e.g., computer-readable media 114, includes digital storage media also termed non-transitory computer-readable media, and/or communication media. Digital storage media includes tangible storage units such as volatile memory, nonvolatile memory, and/or other persistent and/or auxiliary computer storage media, removable and non-removable digital storage media implemented in any method and/or technology for storage of information such as computer-readable instructions, data structures, program modules, and/or other data. Digital storage media includes tangible and/or physical forms of media included in a device and/or hardware component that is part of a device and/or external to a device, including but not limited to RAM, static RAM (SRAM), dynamic RAM (DRAM), phase change memory (PRAM), read-only memory (ROM), erasable programmable read-only memory (EPROM), electrically erasable programmable read-only memory (EEPROM), flash memory, compact disc read-only memory (CD-ROM), digital versatile disks (DVDs), optical cards and/or other optical storage media, magnetic cassettes, magnetic tape, magnetic disk storage, magnetic cards and/or other magnetic storage devices and/or media, solid-state memory devices, storage arrays, network attached storage, storage area networks, hosted computer storage and/or memories, storage, devices, and/or storage media that can be used to store and maintain information for access by a computing device 102 and/or 104.

In contrast to digital storage media also termed non-transitory computer-readable media, communication media can embody computer-readable instructions, data structures, program modules, and/or other data in a modulated data signal, such as a carrier wave, and/or other transitory transmission mechanism. As defined herein, digital storage media does not include communication media.

In some examples, computer-readable media 114 can store instructions executable by the processing unit(s) 112 that, as discussed above, can represent a processing unit incorporated in computing device 102. Computer-readable media 114 can additionally and/or alternatively store instructions executable by external processing units such as by an external central processing unit (CPU) and/or external processor of any type discussed herein. In some examples at least one processing unit 112, e.g., a CPU, graphics processing unit (GPU), and/or hardware logic device, can be incorporated in computing device 102, while in some examples at least one processing unit 112, e.g., one or more of a CPU, GPU, and/or hardware logic device, can be external to computing device 102.

Computer-readable media 114 can store, for example, computer-executable instructions of an operating system 118, module(s) of a nutrient optimization engine 122, and/or other modules, programs, and/or applications that are loadable and executable by processing unit(s) 112. In various examples, computer-readable media 114 can store, computer-executable instructions of a nutritional training engine 120 and/or nutritional model(s) 124, etc. In some examples not shown, one or more of the processing unit(s) 112 in one of the computing device(s) 102 and/or 104 can be operably connected to computer-readable media 114 in a different one of the computing device(s) 102 and/or 104, e.g., via communications interface and network 108. For example, program code to perform steps of flow diagrams herein, e.g., as described herein with reference to nutrient optimization engine 122, can be downloaded from a computing device 102 operating as a server to a computing device 104 operating as a client, e.g., via the network 108, and executed by one or more processing unit(s) in computing device 104. For example, the computer-executable instructions stored on the computer-readable media 114 can upon execution configure a computer such as a computing device 102 and/or 104 to perform operations described herein with reference to the operating system 118, the nutrient optimization engine 122, and in some instances the nutritional training engine 120.

Computer-readable media 114 can also store, for example, one or more nutritional model(s) 124, individually and/or collectively referred to herein with reference 124. When included, nutritional model(s) 124 can include nutritional guidelines and can accommodate varied criteria e.g., one or more specialized diets such as vegetarian, vegan, pescatarian, Mediterranean, ketogenic (keto), kosher, halal, etc., and/or nutritional guidelines tailored to avoid food allergies, e.g., gluten free, peanut free, dairy free, etc., and can be associated with one or more datastore(s) 126. Nutritional models can also be customized, e.g., a vegan diet with allowance for eggs but not dairy. As noted above, the nutritional models 124 can also be associated with a variety of characteristics associated with a user, e.g., family size and/or makeup (infants, children, teens, adults), user age or age range, sex, activity level (sedentary, moderately active, active, athlete), specialty diet(s), food purchase history, customized nutrient guideline, etc. (collectively "parameters") to tailor grocery recommendation(s). In some examples without nutritional model(s) 124, nutritional guidelines can be stored in datastore 126. In at least one example, nutrient optimization engine 122 can perform data analysis and/or processing. In examples including nutritional training engine 120 and nutritional model(s) 124, nutritional training engine 120 and/or the nutrient optimization engine 122 can determine values of parameters compared to nutritional model(s) 124 to perform data analysis and/or processing.

Bus 116, which in some instances can include one or more of a system bus, a data bus, an address bus, a Peripheral Component Interconnect (PCI) Express (PCIe) bus, a PCI bus, a Mini-PCI bus, and any variety of local, peripheral, and/or independent buses, and/or any combination thereof can operably connect one or more processing unit(s) 112 to one or more computer-readable media 114.

Computing device 102 can also include one or more communications interfaces 128 connected via the bus 116 to processing unit(s) 112 to enable wired and/or wireless communications between computing device(s) 102 and other networked computing devices 102 and/or 104 involved in AI assisted technology for grocery recommendations and nutrient optimization, and/or other computing device(s), e.g., over network(s) 108. Such communications interface(s) 128 can include one or more transceiver devices, e.g., network interface controllers (NICs) such as Ethernet NICs and/or other types of transceiver devices, to send and receive communications over a network. The processing unit(s) 112 can exchange data through respective communications interface(s) 128. In some examples, the communications interface 128 can include a PCI Express (PCIe) transceiver, and the network 108 can include a PCIe bus. In some examples, the communications interface 128 can include, but is not limited to, a transceiver for cellular (3G, 4G, 5G, and/or other), WI-FI, Ultra-wideband (UWB), BLUETOOTH, and/or satellite transmissions. The communications interface 128 can include a wired I/O interface, such as an Ethernet interface, a serial interface, a Universal Serial Bus (USB) interface, an INFINIBAND interface, and/or other wired interfaces. The communications interface 128 can additionally and/or alternatively include one or more user-interface devices, buses such as memory buses and/or local buses, memory interfaces, and/or hardwired interfaces such as 0-20 mA control lines. For simplicity, these and other components are omitted from the illustrated computing device 102(3).

As noted above, computer-readable media 114 of the computing device 102 can store an operating system 118. In some examples, an operating system 118 is not used (commonly referred to as a "bare metal" configuration). In some examples, the operating system 118 can include components that enable and/or direct the computing device 102 to receive data via various inputs (e.g., user controls, network and/or communications interfaces, memory devices, and/or sensors), and process the data using the processing unit(s) 112 to generate output. The operating system 118 can further include one or more components that present the output (e.g., display an image on an electronic display, store data in memory, and/or transmit data to another computing device). The operating system 118 can enable a developer or an engineer, to interact with the computing device 102 using a user interface. User interface(s) (UI)s described herein can include one or more of a graphical user interface (GUI), and audio user interface (AUI), and/or various other input/output interfaces generally referenced as UI including touch-input interfaces and the like. Additionally, the operating system 118 can include components that perform various functions generally associated with an operating system 118, e.g., storage management and internal-device management.

In some examples, computing device 102 can include a user interface 130 configured to permit a developer or an engineer responsible for computing device 102(3), distributed computing resources 106, environment 100 and/or an application administrator, to operate the nutrient optimization engine 122 and/or to access the datastore(s) 126. In examples including nutritional training engine 120 computing device 102 can include a user interface 130 configured to permit a developer or an engineer responsible for computing device 102(3), distributed computing resources 106, environment 100 and/or an application administrator, to operate, the nutritional training engine 120 and the model(s) 124, the nutrient optimization engine 122 and/or to access the datastore(s) 126.

Details of an example computing device 104(1) are illustrated at inset 132. The details of example computing device 104(1) can be representative of others of computing device(s) 104. However, each of the computing device(s) 104 can include additional and/or alternative hardware and/or software components. Computing device 104(1) can include one or more processing unit(s) 134 operably connected to one or more computer-readable media 136, e.g., via a bus 138. Some examples of processing unit(s) 134 are discussed above with reference to processing unit(s) 112. Some examples of computer-readable media 136 are discussed above with reference to computer-readable media 114. For example, computer-readable media 136 can include one or more digital storage media or communications media. Some examples of bus 138 are discussed above with reference to bus 116.

Computer-readable media 136 can store, for example, computer-executable instructions of an operating system 140, and/or other modules, programs, and/or applications 142 that are loadable and executable by processing unit(s) 134. Other applications in applications 142 can be operable with nutrient optimization application 144. Some examples of operating system 140 are discussed above with reference to inset 110.

In some examples, the computing device 104 can be configured to communicate with distributed computing resources 106 and/or computing device(s) 102 to query or send information to datastore 126 and/or to operate nutrient optimization engine 122 and/or nutrition model 124. For example, the computing device 104 can transmit a request to distributed computing resources 106 and/or computing device(s) 102 for an output from the nutrient optimization engine 122 based on the nutritional training engine 120 and/or nutritional model 124 in accordance with information from datastore 126, receive a response, and provide a recommendation to address a nutritional opportunity via a user interface 148 based on that response. In some examples, functions described herein can be shared between one or more computing device(s) 102 and one or more computing device(s) 104. For example, the computing device(s) 104 can operate an input layer of one or more neural network(s) and the distributed computing resources 106 and/or computing device(s) 102 can operate one or more hidden layers and/or output layers of one or more neural network(s). In some examples, the computing device(s) 104 can obtain cart parameters and the distributed computing resources 106 and/or computing device(s) 102 can perform optimization on those parameters via an optimization algorithm associated with nutrient optimization engine 122.

Computing device 104 can also include one or more communications interfaces 146 connected via the bus 138 to processing unit(s) 134 to enable wired and/or wireless communications between computing device(s) 104 distributed computing resources 106 and/or and other networked computing devices 102 and/or 104 involved in end-to-end RNN for joint language understanding and dialogue management, and/or other computing device(s), over network(s) 108. Some examples are discussed above with reference to communications interface(s) 128.

Computing device 104 can include a user interface 148. For example, computing device 104(4) can provide user interface 148 to control and/or otherwise interact with nutrient optimization application 144, distributed computing resources 106, and/or computing devices 102. For example, processing unit(s) 134 can receive inputs e.g., typed and/or spoken queries and/or user utterances and/or other input actions associated with grocery shopping such as one or more of online grocery shopping, grocery membership clubs that tie purchases to membership accounts, and/or other shopping experiences, such as smart phone scanning functionalities via user interface 148 and transmit corresponding data via communications interface(s) 146 to computing device(s) 102.

User interfaces 130 and/or 148 can include one or more input devices, integral and/or peripheral to computing device 102 and/or 104. The input devices can be user-operable, and/or can be configured for input from other computing device 102 and/or 104. Examples of input devices can include, e.g., a keyboard, keypad, a mouse, a trackball, a pen sensor and/or smart pen, a light pen and/or light gun, a game controller such as a joystick and/or game pad, a voice input device such as a microphone, voice-recognition device, and/or speech-recognition device, a touch input device such as a touchscreen, a gestural and/or motion input device such as a depth camera, a grip sensor, an accelerometer, another haptic input, a visual input device such as one or more cameras and/or image sensors, a QR code or bar code scanner, and the like. User interfaces 130 and/or 148 can include one or more output devices configured for communication to a user and/or to another computing device 102 and/or 104. Output devices can be integral and/or peripheral to computing device 102 and/or 104. Examples of output devices can include a display, a printer, audio speakers, beepers, and/or other audio output devices, a vibration motor, linear vibrator, and/or other haptic output device, and the like.

Illustrative Processes

The order in which the operations are described in each example flow diagram and/or process is not intended to be construed as a limitation, and any number of the described operations can be combined in any order and/or in parallel to implement each process. Moreover, the operations in each of FIGS. 2 and 3 can be implemented in hardware, software, and/or a combination thereof. In the context of software, the operations represent computer-executable instructions that, when executed by one or more processors, cause one or more processors to perform the recited operations. In the context of hardware, the operations represent logic functions implemented in circuitry, e.g., datapath-control and finite-state-machine sequencing functions.

Figure 2:
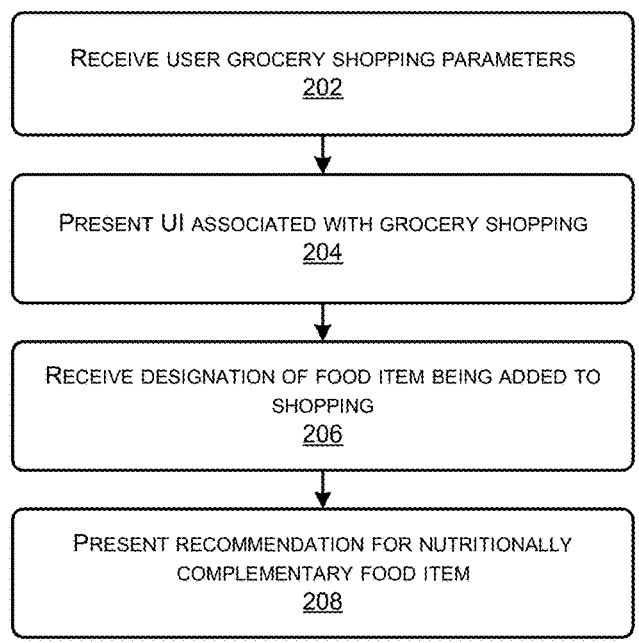
FIG. 2 is a flow diagram that illustrates an example process associated with AI assisted technology for grocery recommendations and nutrient optimization according to various examples described herein.

FIG. 2 is a flow diagram that illustrates an example process 200 of interactions for an intuitive application (app) that can use AI to improve grocery recommendations during grocery shopping to optimize nutrition and encourage users to purchase foods that can help the user receive complete nutrition. The app can capture nutritional information while a user is doing grocery shopping including one or more of: online grocery shopping, using scanning functionality on their smartphone while they shop at a grocery store, and/or from a record of their purchases associated with a membership club, which can help users seeking to improve their health because it can alleviate the need for the users to separately record their consumption whether manually or through an app. In addition, the app can enable users to plan food consumption and optimize their nutrition in advance of purchasing the food, with reference to food that is in stock at a grocer or other food provider, which is not possible with existing food tracking applications. In some examples, the app can include an option for a user to report meals and/or food items acquired without activating the app, e.g., one or more of a restaurant meal, a meal at which the user is a guest, food items acquired from a grocery store without interaction with the app, etc. In some examples, the app can include an option for a user to exclude certain food items from recommendations, e.g., food purchased for someone else, food purchased in bulk, etc.

Example functions shown in FIG. 2 can be implemented by consumer device(s) 104, e.g., using software such as nutrient optimization app 144 running on such device(s). For the sake of illustration, the example process 200 of configuring a device according to an app that can use AI to improve grocery recommendations during grocery shopping to optimize nutrition, e.g., nutrient optimization app 144 is described below with reference to processing unit 134 and other components of consumer device(s) 104 as shown in inset 132, FIG. 1. Consumer device(s) 104 can carry out and/or participate in the steps of the example method. However, other processing unit(s) and/or other components of computing device(s) 102 and/or 104 can carry out step(s) of described example processes such as process 200. Similarly, example method(s) shown in FIG. 2 are also not limited to being carried out by any specifically-identified components.

At block 202, a consumer device 104 with nutrient optimization app 144 installed can receive parameters associated with a user for grocery shopping, including online grocery shopping, using scanning functionality on their smartphone while they shop at a grocery store, and/or from a record of their purchases associated with a grocery membership club. For example, parameters associated with users can include one or more of a user identifier, device identifier, family size and/or makeup (infants, children, teens, adults), user age or age range, sex, activity level (sedentary, moderately active, active, athlete), specialty diet(s), food purchase history, storage authorization, registration information, customized nutrition guideline, etc. In various examples, a food item is a source of energy to a consumer, wherein the energy is measured in kilocalories (referred to herein as "Calories"). A kilocalorie is the amount of heat needed to raise the temperature of one kilogram of water by one degree Kelvin or Celsius. In examples, a food item can include various nutrients, such as vitamins, minerals, fiber, macronutrients, probiotics, and/or bacteria as set forth above.

At block 204, consumer device 104 with nutrient optimization app 144 installed can present an output UI, e.g., a GUI or AUI associated with grocery shopping via an output interface associated with the consumer device, e.g., UI 148 of device 104.

At block 206 a consumer device 104 can receive designation of a food item being added, for example to an online shopping cart, smart phone scanning functionalities, and or the like, via an input interface such as a touch interface, a keypad, a microphone, etc.

At block 208 a consumer device 104 can present a recommendation for a nutritionally complementary food item via an output UI. In at least one example, the nutritionally complementary food item can be identified based on nutritional information associated with the designated food item and nutritional information associated with other food items in a shopping cart such as one or more of an online grocery shopping cart, grocery membership clubs' records, and/or smart phone scanning functionalities. In at least one example, the recommendation can include to reduce a nutritional deficit for a first nutrient relative to the nutritional guideline for the first nutrient while minimizing a nutritional surplus for a second nutrient relative to the nutritional guideline.

In various examples, the recommendation can be presented responsive to designation of the food item being added to the cart at block 206 and before another food item is designated for addition to the cart. In some examples, to cause less interruption of the user's shopping experience, the recommendation can be presented responsive to a discrete number of food items being designated for addition to the cart. In various example, the recommendation can be presented responsive to receiving an indication that the shopping session is concluding such as receiving a request to check out. The latter examples can provide the least interruption to the user's shopping experience, but they may also not be as effective in encouraging purchase of complementary food items. Settings related to recommendation timing and other aspects of nutrient optimization app 144 can be controlled by one or more of an application administrator, licensor, a food item sponsor or promoter, a grocery shopping partner, and/or the user in various examples.

In some examples nutrient optimization app 144 can offer an opportunity for a user to register the app including authorization to store parameters associated with the user like family size and/or makeup (infants, children, teens, adults), user age or age range, sex, activity level (sedentary, moderately active, active, athlete), specialty diet(s), food purchase history, and/or dietary restrictions/allergies, customized nutrition guideline, etc. In such examples, the user may be able to opt in or opt out of: registration, storing parameters, and/or sharing any personally identifiable information. In situations where a user opts out of registering or authorizing the nutrient optimization app 144 to store parameters, the nutrient optimization app 144 can provide recommendations for complementary food item(s) based on general nutritional guidelines, which may not be as beneficial or relevant to the user. In situations where a user opts in to registering and authorizing the nutrient optimization app 144 to store parameters, the nutrient optimization app 144 can anonymize personally identifiable information associated with the user that will be maintained as part of a user record.

In various examples in which a user has opted in to registering and authorizing the nutrient optimization app 144 to store parameters, the nutrient optimization app 144 can receive an indication of a food purchase and can cause an indication of a food purchase to be added to (or omitted from) the user record. In examples, nutrient optimization app 144 can use such previous purchase information to improve recommendations of complementary food items for the associated user.

Figure 3:
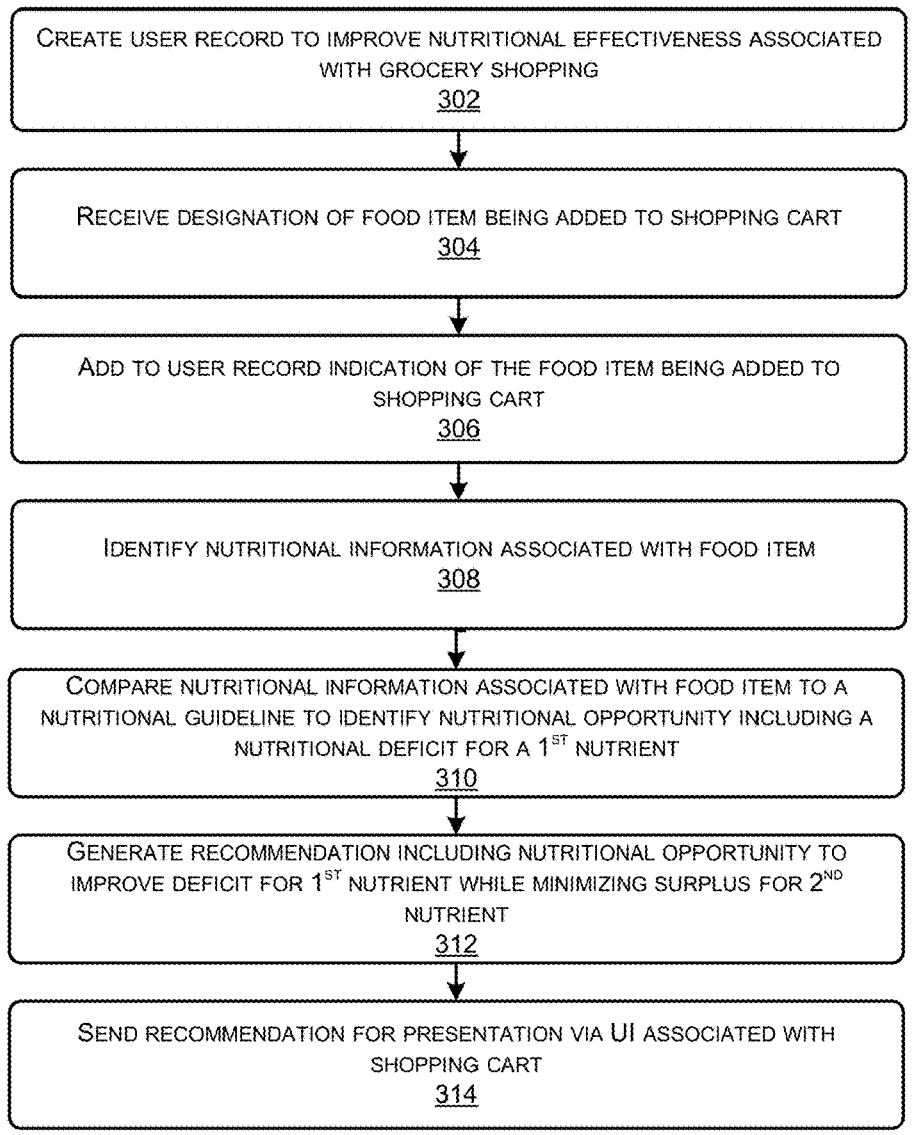
FIG. 3 is a flow diagram that illustrates an example process associated with AI assisted technology for grocery recommendations and nutrient optimization according to various examples described herein.

Example functions shown in FIG. 3 and example processes described herein can be implemented by distributed computing resources 106 on and/or otherwise embodied in one or more computing device(s) 102 and/or 104, e.g., using software running on such device(s). For the sake of illustration, the example process 300 is described below with reference to processing unit 112 and other components of computing device 102 as shown in inset 110, FIG. 1, which can carry out and/or participate in the steps of the example method. However, other processing unit(s) such as processing unit 112 and/or other components of computing device(s) 102 and/or 104 can carry out step(s) of described example processes such as process 300. Similarly, example method(s) shown in FIG. 3 are also not limited to being carried out by any specifically identified components.

FIG. 3 is a flow diagram that illustrates example processes for AI assisted nutritional optimization according to various examples described herein.

At block 302, one or more parts of a system including a computing device 102 configured to implement nutritional optimization as described herein can create a user record associated with a user for grocery shopping. In some examples, the user record can include stored parameters associated with a user and can include one or more of a user identifier, device identifier, family size and/or makeup (infants, children, teens, adults), user age or age range, sex, activity level (sedentary, moderately active, active, athlete), specialty diet(s), food purchase history, storage authorization, registration information, customized nutrition guideline, etc.

At block 304, one or more parts of a system including a computing device 102 configured to implement nutritional optimization as described herein can receive a designation corresponding to addition of a food item to a grocery shopping cart such as one or more of an online grocery shopping cart, smart phone scanning functionalities, and the like. In some examples, the designation can take place via a standalone app. In various examples, the designation can be received via an API for one or more other apps such as grocery shopping apps and/or delivery apps. In some examples, the designation can be received via a browser extension and can be activated when the browser navigates to an online grocery portal or meal subscription service. In examples, designations associated with a particular user can occur through any combination of these examples, such as both from another app and a browser, etc. In various examples, the system can make these designations available to nutrient optimization engine 122 to apply nutritional model(s) 124. In some examples, the system can store these designations in datastore(s) 126.

At block 306, one or more parts of a system including a computing device 102 configured to implement nutritional optimization as described herein can add to the user record or update the user record in datastore(s) 126 with an indication of the food item designated for addition to the shopping cart, such as one or more of an online grocery shopping cart, via a smart phone scanning functionalities to scan items while shopping, and the like. In various examples, the user record, which can include grocery membership club account information, can be updated with this information at a variety of times such as when the consumer device is connected to a particular type of network, periodically, e.g., once a week, each night, etc., responsive to the user completing a grocery shopping session, and/or immediately upon addition of the food item to the shopping cart, e.g., online shopping cart, via smart phone scanning functionality while shopping, etc. or a combination of any of these times. One of more of these time settings can be controlled by one or more of an application administrator, licensor, a food item sponsor or promoter, grocery shopping partner, and/or the user in various examples.

At block 308, one or more parts of a system including a computing device 102 configured to implement nutritional optimization as described herein can identify nutritional information associated with the food item. In examples the system can identify a record from a food datastore, e.g., in datastore(s) 126, associated with the food item designated for addition to the shopping cart. The record associated with the food item can include nutritional information associated with the food item such as serving size and/or nutrient content including one or more of calcium, cholesterol, carbohydrates, vitamin A, vitamin C, vitamin D, fiber, iron, potassium, protein, saturated fat, sugar, sodium, etc.

At block 310, one or more parts of a system including a computing device 102 configured to implement nutritional optimization as described herein can compare nutritional information associated with the food item designated for addition to the shopping cart to one or more nutritional guideline(s), which can be stored in datastore(s) 126. In some examples, the one or more nutritional guideline(s) can include a specialized nutritional guideline and/or a nutritional guideline tailored to avoid food allergies. Based on the comparison, nutrient optimization engine 122 can identify one or more nutritional opportunities related to the food item or food items in the shopping cart. In various examples, a nutritional opportunity can include a nutritional deficit relative to the referenced nutritional guideline(s) for at least one nutrient and/or a nutritional surplus relative to the reference nutritional guideline(s) for at least one nutrient.

At block 312, one or more parts of a system including a computing device 102 configured to implement nutritional optimization as described herein can generate a recommendation including, relative to the referenced nutritional guideline(s), the nutritional opportunity to improve the deficit for a nutrient while minimizing a surplus for another nutrient. In the example illustrated in FIGS. 4A and 4B and discussed below, the nutritional opportunity is to improve a deficit in potassium and fiber while minimizing surpluses in vitamin A, vitamin C, and sugar.

At block 314, one or more parts of a system including a computing device 102 configured to implement nutritional optimization as described herein can send an indication of a recommendation for presentation via a user interface 148, e.g., a GUI associated with the nutrient optimization app 144 and/or the shopping cart. Several examples are illustrated in FIGS. 4A and 4B and discussed below.

Illustrative Graphical User Interface

Figure 4A:
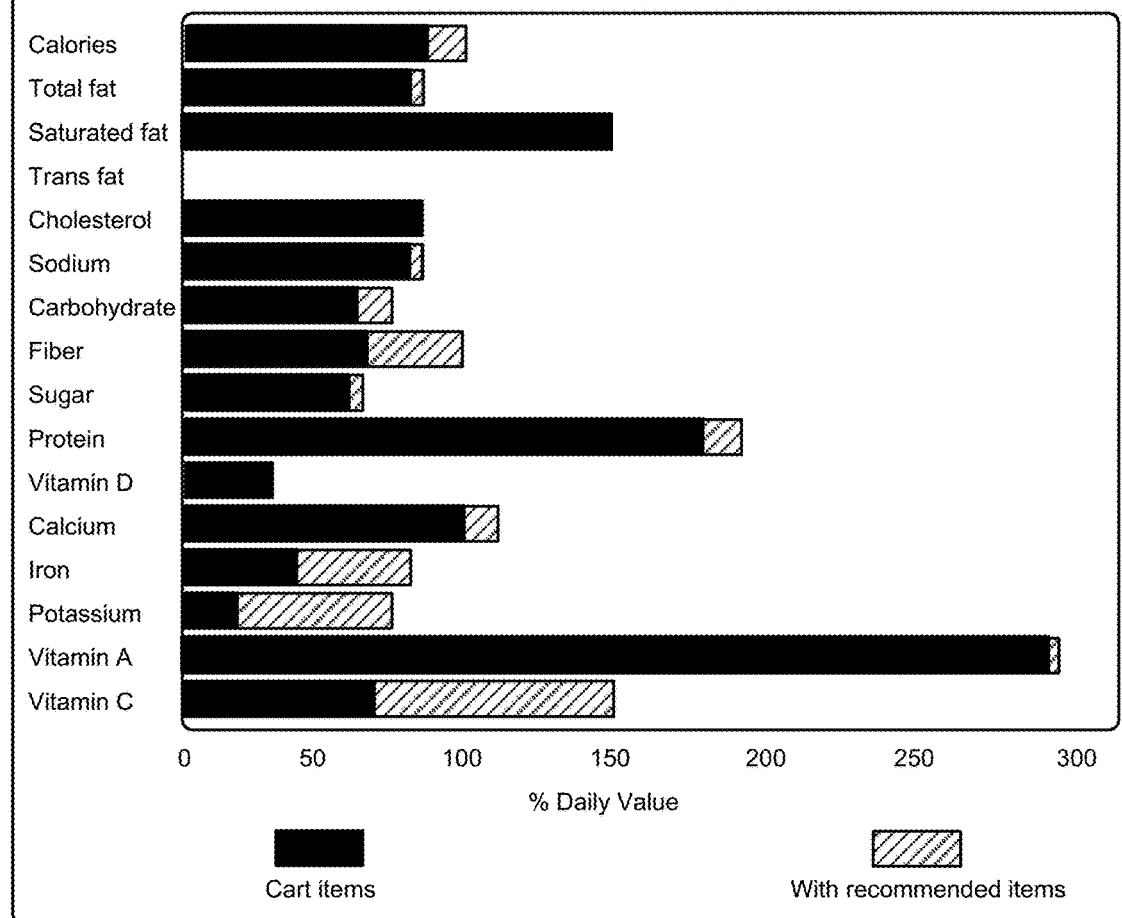
FIG. 4A illustrates part of an example graphical user interface (GUI) associated with AI assisted technology grocery recommendations and nutrient optimization according to various examples described herein.

FIG. 4A is an illustrative diagram that shows parts of one or more example graphical user interface(s) (GUIs) 400, 400(1) that can be presented by consumer device(s) 104. The illustration includes a shopping cart 402, which in the illustrated example includes the food items apples, chicken breast, lettuce, broccoli, brown rice, steak, carrots, cheddar cheese, and almond milk, though many other options are possible and to be expected. In the illustrated example, the food items presented, i.e., almond milk and steak, can represent what the user actually selected for addition to their cart and/or a more general representation of what the user selected. That is, in some examples, the general representations almond milk and steak can represent selections made by the user, and the particular food items added to the cart can be based on the user's previous purchases. Alternatively, in some examples, the general representations almond milk and steak can represent more specific and/or branded selections of vanilla almond milk and steak strips.

The illustration includes a presentation of recommended items 404, which in the illustrated example include salt-free seasoning, organic young jackfruit, and potatoes. The recommended items are based at least in part on the contents of the shopping cart 402. In some examples, the particular products recommended can be based on one or more of a user's previous purchases, inventory of the particular grocery store(s), food item(s) that are sponsored or promoted by one or more advertiser(s)/sponsor(s) or the grocery store partner(s), etc. In various examples, the recommended items can be presented via text, image, audio, a link to purchase the item, etc., or any combination thereof.

The illustration includes a graphical representation of total nutrients 406, which in the illustrated example include a plurality of bar graphs corresponding to nutritional information and a plurality of nutrients from the food items in the shopping cart 402; in some examples, a pie chart presentation may be selected or shown in place of the bar graphs. As shown, the bar graphs reference a percentage (%) of recommended daily value for the respective nutritional information and nutrients and the bar graphs show the change that would take place with the addition of the recommended items to the shopping cart. For example, the bar graphs show that the number of Calories in the cart are less than 100% of the recommended daily value, which would be met with the addition of the recommended items while the amount of vitamin A present in the foods in the cart represents a surplus relative to the other amount of the other items—almost 300% of the recommended daily value, or almost 3 days' worth of vitamin A. Thus, nutritional optimization app 144 can highlight to users when the food items in the cart represent a nutritional opportunity indicating a surplus, in the illustrated instance particularly of vitamin A, protein, and saturated fat. In some examples nutritional optimization app 144 can highlight to users when the food items in the cart represent a nutritional opportunity indicating a surplus of Calories, fat, sodium, or any of the tracked nutrients. In various examples, elements 402, 404, and/or 406 can be presented in separate locations, or separate screens, and/or via pop-up windows, etc. In some examples, element 402 and/or 406 can be omitted and/or element 404 may indicate that no recommendations are available. In some examples, element 406 (or another interface) can include a GUI that can enable the user to customize parameters such as food items included in the summary, which nutrient contents to display, etc.

FIG. 4B is an illustrative diagram that shows another part of an example graphical user interface (GUI) 400, 400(2) that can be presented by consumer device(s) 104. The illustration includes a table 408 of detailed nutrient values in percentage of recommended daily value for the food items from shopping cart 402 and recommended items 404, FIG. 4A. In various examples, table 408 can be presented in separate location or on a separate screen from none, any, or all of elements 402, 404, and/or 406, and/or via a pop-up window, etc. In the illustrated example the food items are brown rice, vanilla almond milk (which was simply shown as "almond milk" in shopping cart 402), broccoli, steak strips (which was simply shown as "steak" in shopping cart 402), apples, carrots, cheddar cheese, lettuce, chicken breast, salt free seasoning, organic young jack fruit, and potatoes, though many other options are possible and to be expected. In the illustration, the food items are presented across the top of the table, while nutrients: Calories, total fat, saturated fat, trans fat, cholesterol, sodium, carbohydrate, fiber, sugars, protein, vitamin D, calcium, iron, potassium, vitamin A, and vitamin C are presented on the left side of the table. Of course, alternative presentations are possible. In the illustrated example, the more detailed food items presented, i.e., vanilla almond milk and steak strips, can represent what the user actually selected for addition to their cart and/or the user may have selected the more general representations almond milk and steak, and the food items shown may be based on the user's previous purchases.

Corresponding to the bar graphs, 406, the table 408 provides the underlying values to show how the addition of the recommended items salt free seasoning, organic young jack fruit, and potatoes address the nutritional opportunities of deficits in potassium, Vitamin C, and fiber while also minimizing the nutritional opportunities of surpluses of vitamin A, protein, saturated fat, or Calories. In various examples, the recommended daily value percentage(s) for table 408 can be optimized according to user parameters. In some examples, table 408 can be omitted from GUI 400.

Illustrative Components

Figure 5:
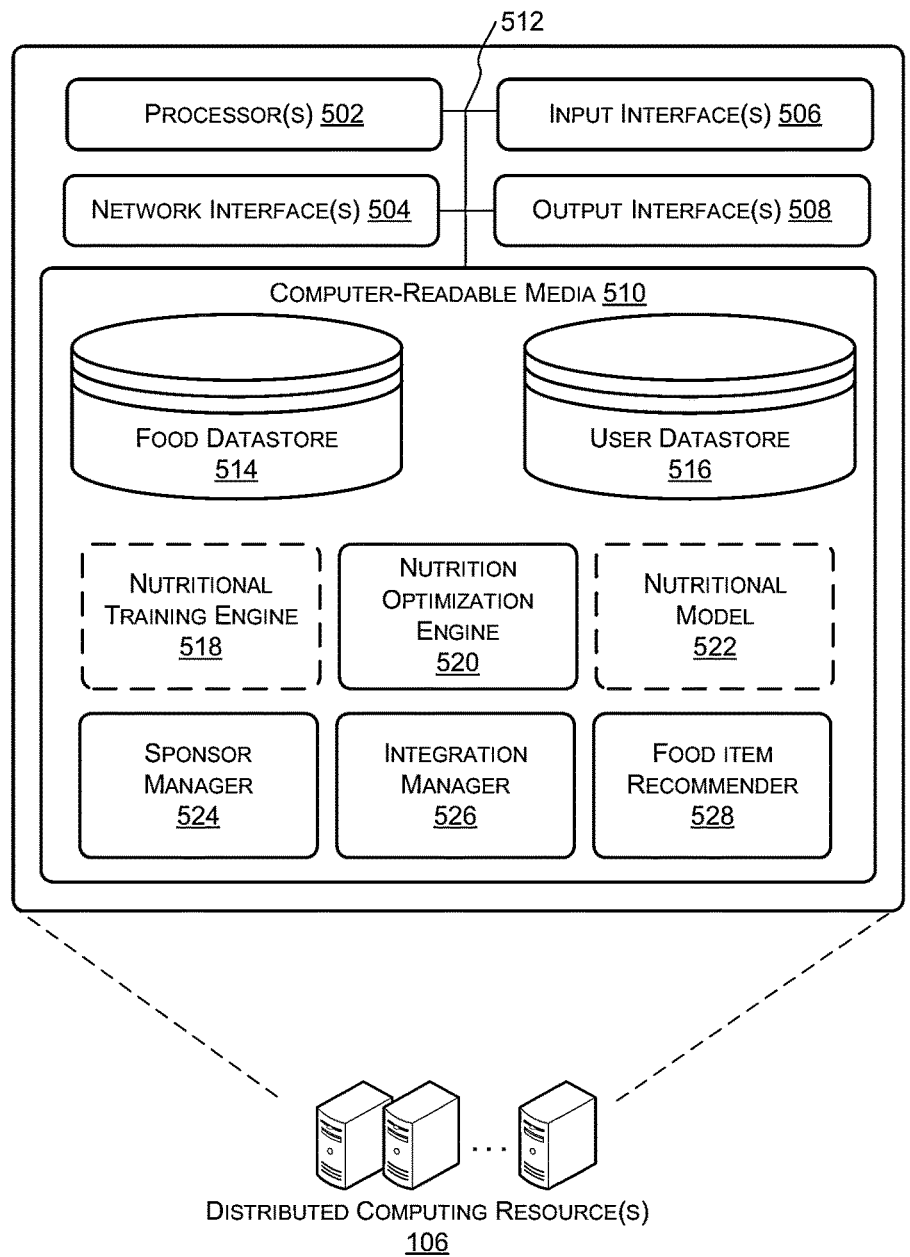
FIG. 5 is a block diagram depicting an example computing device configured to participate in AI assisted technology for grocery recommendations and nutrient optimization according to various examples described herein.

FIG. 5 is an illustrative diagram that shows an example configuration of components of a computing device 500, which can represent a computing device(s) 102, and which can be and/or implement a training and/or operation system, device, and/or apparatus, according to various examples described herein. Example computing device 500 includes one or more processing unit(s) 502, network interface(s) 504, input interface(s) 506, output interface(s) 508, and computer-readable media 510. The components of computing device 500 are operatively connected, for example, via a bus 512. These components can represent corresponding components from device(s) 102 *a*, e.g., processing unit(s) 502 can represent processing unit(s) 112, bus 512 can represent bus 116, etc.

In example computing device 500, processing unit(s) 502 can correspond to processing unit(s) 112, and can represent, for example, a CPU-type processing unit, a GPU-type processing unit, a field-programmable gate array (FPGA), another class of digital signal processor (DSP), or other hardware logic components that may, in some instances, be driven by a CPU. For example, and without limitation, illustrative types of hardware logic components that can be used include Application-Specific Integrated Circuits (ASICs), Application-Specific Standard Products (ASSPs), System-on-a-chip systems (SOCs), Complex Programmable Logic Devices (CPLDs), etc. In some examples, processing unit(s) 502 can include an on-board memory, e.g., a RAM and/or cache, not shown.

Network interface(s) 504, which can represent communications interface(s) 128, can represent, for example, network interface controllers (NICs) or other types of transceiver devices to send and receive communications over a network.

Input/output (I/O) interfaces 506 and 508 allow computing device 500 to communicate with input/output devices such as user input devices including peripheral input devices (e.g., a keyboard, a mouse, a pen, a game controller, a voice input device, a touch input device, a gestural input device, and the like) and/or output devices including peripheral output devices (e.g., a display, a printer, audio speakers, a haptic output, and the like).

Computer-readable media 510 can correspond to computer-readable media 124 and can store instructions executable by the processing unit(s) 502. Computer-readable media 510 can also store instructions executable by external processing units such as by an external CPU, an external GPU, and/or executable by an external accelerator, such as an FPGA type accelerator, a DSP type accelerator, or any other internal or external accelerator. In various examples, at least one CPU, GPU, and/or accelerator is incorporated in computing device 200, while in some examples one or more of a CPU, GPU, and/or accelerator is external to computing device 500.

In the illustrated example, computer-readable media 510 includes two data stores, food datastore 514 and user datastore 516, which can also be represented by datastore 126, FIG. 1. In various examples, food datastore 514 and/or user datastore 516 can include data storage such as a database, data warehouse, or other type of structured or unstructured data storage (e.g., a Structured Query Language, SQL, and/or NoSQL database), etc. In some examples, food datastore 514 and/or user datastore 516 can include a corpus and/or a relational database with one or more tables, indices, stored procedures, and so forth to enable data access including one or more of hypertext markup language (HTML) tables, resource description framework (RDF) tables, web ontology language (OWL) tables, and/or extensible markup language (XML) tables, for example. Food datastore 514 and/or user datastore 516 can store data for the operations of processes, applications, components, and/or modules stored in computer-readable media 510 and/or executed by processing unit(s) 502 and/or accelerator(s).

Computing device 500 can implement a nutritional optimization engine 520, which generally operates online and can represent nutritional optimization engine 122, FIG. 1. In examples including a nutritional training engine, computing device 500 can implement a nutritional training engine 518, which generally performs training offline and can represent nutritional training engine 120, FIG. 1. In some examples, nutritional training engine 518 operates on initial input associated with a grocery shopping experience, e.g., selections, typed and/or spoken queries, scans, etc. In some examples, nutritional training engine 518 can operate on initial input, and nutritional optimization engine 520 can operate on ongoing input. Computing device 500 can also implement a nutritional model 522, which is generally updated incrementally and can represent nutritional model 124, FIG. 1. Computing device 500 can include and/or be included in a system and/or device for training and/or operating a neural network and/or other computational model as described herein.

Nutritional optimization engine 520 and/or other modules, can in various examples, scrape nutritional information from a variety of sources like food manufacturer websites, online grocery sites, and the like. Nutritional optimization engine 520 can, in various examples, aggregate nutritional information for food item(s) in a grocery cart. In at least one example, the nutritional optimization engine 520 can represent the nutritional information associated with each food item (nutrient(s) and amount of the nutrient(s) associated with the food item) in the cart in percentage of recommended daily value or convert the nutritional information associated with each food item in the cart to percentage of recommended daily value, and then aggregate the percentages of recommended daily values for the nutrients from the food item(s) represented in the cart. In some examples, the nutritional optimization engine 520 can represent the nutritional information associated with each food item in the cart in identified units of measure, aggregate the units associated with each food item in the cart, and then convert the aggregated values to determine the percentage of recommended daily values for the nutrients from the food items represented in the cart. In some examples, the nutritional information for different food items can be represented in different serving sizes as selected by a user, e.g., by serving, by package size, in bulk, etc.

Nutritional optimization engine 520, in various examples, can calculate a value to represent a nutritional deviation associated with food items in the cart, the deviation being from a perfect balance of nutrients relative to a nutritional guideline. In some examples, the perfect balance of nutrients can be dependent on a user's recommended nutritional intake. In some examples, the deviation value calculation can incorporate a user's previous purchase history in addition to the current cart items. This deviation value, in various examples, can be calculated as a sum of the squared difference between a goal nutrient amount and cart nutrient amount, over all nutrients (equation 1). In some examples, the goal nutrient amount can be the daily recommended value (such as 100% DV), maximum nutrient amount among all nutrient values in a cart, the mean nutrient amount of all nutrients in a cart, etc. In some examples, the deviation value can be calculated based on select nutrients and not all possible nutrients, which can be customized by the user.

$$\text{Deviation value} = \Sigma_{n=1,2,\ldots,N}(\text{goal}_n - x_n)^2 \quad \text{(Equation 1)}$$

Where n is a nutrient 1 to N (e.g., Calories, fat, sodium, etc.), x is the amount of nutrient in the cart, g is amount of goal nutrient.

In some examples, nutrition optimization engine 520 can use an optimizer to search through a food datastore relevant to the user's parameters and cart contents, e,g, food datastore 514, to find a food item or food category for recommendation that, if added to current cart items, would decrease and minimize the cart deviation. In some examples, the optimizer used can include greedy search, embedded conic solvers, commercial optimization solvers such as GUROBI, etc. In some examples, multiple food items can be interchangeable and similarly minimize cart deviation—in this case, the recommended food item or category found by the nutrition optimization engine can be input into the sponsor manager 524 and/or integration manager 526 (and/or nutritional model 522) for further processing. In some examples, nutrition optimizer engine 520 can perform multiple levels of optimization, which can improve efficiency. For example, nutrition optimizer engine 520 can first recommend a food category that best improves overall nutrition for the food items represented in the cart, and second recommend a specific food item, e.g., nutrition optimizer engine 520 can first recommend that the food category that best improves overall nutrition for food items represented in the cart is a category of food items that are high in both vitamin A and vitamin K, and second recommend a specific food item kale.

In some examples, computer-readable media 510 of the computing device 500 can represent computer-readable media 114, FIG. 1, and can store a plurality of modules associated with the nutritional optimization engine 520, (and/or the nutritional training engine 518 and the nutritional model 522), to enable a nutritional optimization app like nutritional optimization app 144. Processing unit(s) 502 can be configured to execute modules of the plurality of modules. For example, the computer-executable instructions stored on the computer-readable media 510 can, upon execution, configure a computer such as a computing device 500 to perform operations described herein with reference to modules such as sponsor manager module 524, integration manager module 526, and/or food item recommender module 528, which are discussed below.

Nutritional model 522 and/or a nutrional guideline and/or user record can, in various examples, include a seasonal model that can take temperature or weather for a geographical location associated with the user into account either from historic information or by accessing weather forecast data. For example, the nutritional model 522, nutrional guideline, and/or user record incorporating a seasonal model can cause changes in the types of food items recommended as complementary food items such as biasing to recommend seasonal produce or hot foods, e.g., soups (or ingredients to make soup), when temperatures are relatively cold for the geographical location and cold foods, e.g., salads (or ingredients to make salads), when temperatures are relatively hot for the geographical location. In some examples, nutritional model 522, nutrional guideline, and/or user record can include a personalization model that can take a particular user's purchase history into account. For example, the nutritional model 522, nutrional guideline, and/or user record incorporating a personalization model can cause changes in the types of food items, brands of food items, and/or amounts of food items recommended as complementary food items such as biasing to recommend food items with a later use-by date and/or more food items for users that shop relatively infrequently and/or biasing to previously purchased brands and/or alternatives of similar cost to previously purchased brands, e.g., recommend premium substitutions for premium brands that are not available and low-cost substitutions for low-cost brands that are not available. In some examples, nutritional model 522, nutrional guideline, and/or user record can employ a convolutional neural network, a recursive neural network, a recurrent neural network, etc. to learn and optimize nutritional information.

Sponsor manager module 524 can, in various examples, enable nutrition optimization engine 520 (and/or nutritional model 522) to accept information related to one or more sponsors or promoters and associated product(s) as parameters. Sponsor manager module 524 can cause particular brands of products to be presented or to be presented first by food item recommender 528, such as in the recommended items 404.

Integration manager module 526 can, in various examples, enable nutrition optimization engine 520 (nutritional model 522) to integrate information related to one or more of a food item sponsor or promoter, a grocery shopping partner, such as one or more of grocery stores, grocery membership clubs, and/or other shopping experiences with nutritional information from nutritional guidelines, and/or user parameters, etc. to produce optimized nutritional opportunities that can help the user receive complete nutrition. In at least one example, the app can participate in or broker payments associated with grocery shopping including one or more of charging the user a fee to customize grocery recommendations based on dietary preferences and purchase history, charging grocery providers a fee to access the API so their shoppers can have access to recommendations that improve nutrition, charging sponsors a fee to have their product prioritized in recommendations for a specific food category, charging a grocery retailer a percentage of their increased sales revenue due to the app recommendations, etc. In some examples such fees can be on-demand fees, periodic fees, subscription fees, etc.

Food item recommender module 528 can, in examples, produce one or more recommended food items according to the operations of the nutrition optimization engine 520 and/or the integration manager 526. The food item recommender module can generate the list of food items to be presented via a UI associated with the nutrient optimization app 144. In some examples, the particular products recommended can be based on one or more of a user's previous purchases, inventory of the particular grocery store(s), food item(s) that are sponsored or promoted by one or more advertiser(s) or the grocery store partner(s), etc.

Computing device 500 can exchange data with computing devices 102 and/or 104 (e.g., servers, desktop computers, laptop computers, hybrid computing devices, tablet computers, smart phones, etc.) via one or more network(s) 108, such as the Internet. In some examples, computing device 500 can receive data from one or more data source(s) (not shown) via one or more network(s) 108. Example data source(s) can include computing devices 102 and/or 104, sensors, data aggregators, and/or data feeds, e.g., via application programming interfaces (APIs). The processing units 502 can retrieve data from the data source(s), e.g., via an HTTP request such as a GET to a Web Services and/or Representational State Transfer (REST) API endpoint.

CONCLUSION

Although the techniques have been described in language specific to structural features and/or methodological acts, it is to be understood that the appended claims are not necessarily limited to the features and/or acts described. Rather, the features and acts are described as example implementations of such techniques. For example, network 108, processing unit(s) 112/134/502, and other structures described herein for which multiple types of implementing devices or structures are listed can include any of the listed types, and/or multiples and/or combinations thereof.

The operations of the example processes are illustrated in individual blocks and summarized with reference to those blocks. The processes are illustrated as logical flows of blocks, each block of which can represent one or more operations that can be implemented in hardware, software, and/or a combination thereof. In the context of software, the operations represent computer-executable instructions stored on one or more computer-readable media that, when executed by one or more processors, enable the one or more processors to perform the recited operations. Generally, computer-executable instructions include routines, programs, objects, modules, components, data structures, and the like that can configure a processor to perform particular functions and/or implement particular abstract data types. The order in which the operations are described is not intended to be construed as a limitation, and any number of the described operations can be executed in any order, combined in any order, subdivided into multiple sub-operations, and/or executed in parallel to implement the described processes. The described processes can be performed by resources associated with one or more computing device(s) 102, 104, and/or 500 such as one or more internal and/or external CPUs and/or GPUs, and/or one or more pieces of hardware logic such as FPGAs, DSPs, and/or other types described above.

All of the methods and processes described above can be embodied in, and fully automated via, software code modules executed by one or more general-purpose computer(s) and/or processor(s) thereby reconfiguring the general-purpose computer(s) and/or processor(s) as special purpose computer(s) and/or processor(s) during their execution. The code modules can be stored in any type of computer-readable storage medium and/or other computer storage device. Some and/or all of the methods can be embodied in specialized computer hardware.

Conditional language such as, among others, "can," "could," "might" and/or "may," unless specifically stated otherwise, are understood within the context to present that certain examples include, while other examples need not include, certain features, elements and/or steps. Thus, such conditional language is not generally intended to imply that certain features, elements and/or steps are in any way required for one or more examples and/or that one or more examples necessarily include logic for deciding, with and/or without user input and/or prompting, whether certain features, elements and/or steps are included and/or are to be performed in any particular example. The word "or" is used herein in an inclusive sense unless specifically stated otherwise. Accordingly, conjunctive language such as the phrases "X, Y, or Z" or "at least one of X, Y or Z," unless specifically stated otherwise, is to be understood as signifying that an item, term, etc., can be either X, Y, or Z, or any combination thereof.

Any routine descriptions, elements and/or blocks in the flow diagrams described herein and/or depicted in the attached figures should be understood as potentially representing modules, segments, and/or portions of code that include one or more executable instructions for implementing specific logical functions and/or elements in the routine. Alternative implementations are included within the scope of the examples described herein in which elements and/or functions can be deleted and/or executed out of order from any order shown or discussed, including substantially synchronously and/or in reverse order, depending on the functionality involved as would be understood by those skilled in the art. It should be emphasized that many variations and modifications can be made to the above-described examples, the elements of which are to be understood as being among other acceptable examples. All such modifications and variations are intended to be included herein within the scope of this disclosure and protected by the following claims. Moreover, in the claims, any reference to a group of items provided by a preceding claim or clause is a reference to at least some and not necessarily all of the items in the group of items, unless specifically stated otherwise.

What is claimed is:

1. A system comprising:
a processor, in a user device, configured to operate according to a computer readable medium having thereon computer-executable components that include: a nutrient optimization engine, a sponsor module, a seasonal model, an integration module, and a recommender module;
a food datastore including records associated with a plurality of food, the records including nutritional information associated with each of the plurality of food;
a user datastore including records associated with nutritional guidelines according to parameters including at least two of age, sex, specialty diet, customized nutritional guideline, and activity level, wherein the user datastore includes a user nutritional profile associated with a user identifier and based on designated parameters;
a parameter interface, operated by the processor, configured to receive the designated parameters associated with the user identifier;
a purchase interface, operated by the processor, configured to receive an indication of food designated for purchase;
a GUI, operated by the processor and being on the user device, the GUI including:
a first text box for one or more food items designated for purchase, and
a second text box for one or more food items being recommended; and
an input device disposed in the user device, the input device being operated by the processor, configured to receive an input associated with a food item via the GUI,
wherein the processor is configured to:
create a user record associated with the user identifier, wherein the user record includes a nutritional guideline determined based on the designated parameters;
receive at least a first input and a second input associated, respectively, with a first food item and a second food item from the input device via the GUI;
add the first food item and the second food item to the one or more food items designated for purchase;
select a record from the records associated with the plurality of food corresponding to each of the one or more food items designated for purchase, and
instruct the nutrient optimization engine to:
aggregate nutritional information in the selected record;

compare the aggregated nutritional information to the user nutritional profile to identify one or more nutritional opportunities; and
select one or more food items from the plurality of food in the food datastore to provide the one or more nutritional opportunities by the following:
  (1) for each nutrient of each of the one or more food items designated for purchase, calculating a ratio by dividing a serving size of the designated food item for purchase by a serving size of a corresponding item in the plurality of food,
  (2) multiplying each calculated ratio of (1) by an amount of a respective nutrient in the plurality of food to obtain a first value of each nutrient for each one or more food items designated for purchase,
  (3) summing the first value of (2) for each nutrient to obtain a total value of each nutrient in the one or more food items designated for purchase,
  (4) respectively dividing the total value of (3) of each nutrient by a daily consumption amount for the nutrient to obtain a second value, the daily consumption amount being retrieved, by the processor, from the user datastore,
  (5) dividing the second value of (4) by a number of caloric days the one or more food items designated for purchase can supply,
  (6) obtaining a percent of daily consumption amount for each nutrient that is fulfilled by the one or more food items designated for purchase, and creating a sum based on the percent of daily consumption amount to obtain a nutrient deviation score,
  (7) selecting one or more food items from the plurality of food in the food datastore and adding the selected one or more food items to the one or more food items designated for purchase to create a hypothetical combination of food items designated for purchase, and repeating (1)-(6) to obtain a new deviation score of the nutrient deviation score,
  (8) repeating (7) for a plurality of combinations of items in the plurality of food in the food datastore, and ranking obtained new deviation scores for each combination of items from the plurality of food in the food datastore with the one or more food items designated for purchase;
instruct the sponsor module to select one or more food items from the plurality of food in the food datastore provided by a sponsor;
instruct the seasonal model to receive weather data, and select one or more food items from the plurality of food in the food datastore based on the received weather data;
instruct the integration module to select one or more recommended food items based on aggregating the one or more food items selected by the nutrient optimization engine, the sponsor module, and the seasonal model; and
assign the one or more recommended food items to a recommendation; and
instruct the recommender module to send an indication of the recommendation for presentation via the GUI by instructing the GUI to include the recommendation, provided by the recommender module, in the second text box.

2. The system as claim 1 recites, further comprising an interface to receive information to create a record associated with a food item that does not have an associated record.

3. The system as claim 1 recites, further comprising an interface to receive registration of a user to store designated parameters associated with the user and the first food item and second food item designated for purchase.

4. The system as claim 3 recites, wherein the computer-executable instructions further configure the processor to maintain the user record in the user datastore according to registration of the user and to add information to the user record associated with a purchase as previous purchase information.

5. The system as claim 1 recites, wherein the nutritional opportunity includes at least one of a nutritional deficit or a nutritional surplus relative to the nutritional guideline.

6. The system as claim 5 recites, wherein the nutritional opportunity includes the nutritional deficit relative to the nutritional guideline for the specialty diet and the recommendation optimizes at least one nutrient according to the specialty diet.

7. The system as claim 1 recites, wherein the nutritional opportunity includes a nutritional deficit for a first nutrient relative to the nutritional guideline including a goal for the first nutrient and the recommendation includes a food with at least an amount of the first nutrient to improve or eliminate the nutritional deficit for the first nutrient that will minimize a nutritional surplus for a second nutrient relative to the nutritional guideline.

8. The system as claim 1 recites, wherein the recommendation includes a recommended additional food item to improve the nutritional opportunity relative to the nutritional guideline.

9. The system as claim 8 recites, wherein the computer-executable instructions further configure the processor to:
  maintain the user record in the user datastore according to registration of the user;
  add information to the user record associated with a purchase as previous purchase information; and
  wherein the recommendation is based on previous purchase information from the user record.

10. The system as claim 1 recites, wherein the recommendation includes a recommendation to remove or replace a food item designated for purchase to improve the nutritional opportunity relative to the nutritional guideline.

11. The system of claim 1, wherein the input device includes at least one of a touch screen, a camera scanner, or an API.

12. A method comprising:
  creating a user record associated with a user identifier, wherein the user record includes a nutritional guideline determined based on designated parameters;
  receiving at least a first input and a second input associated, respectively, with a first food item and a second food item from an input device via a GUI,
  adding the first food item and the second food item to one or more food items designated for purchase;
  selecting a record from records associated with a plurality of food corresponding to each of the one or more food items designated for purchase;
  instructing a nutrient optimization engine to:
    aggregate nutritional information in the selected record;
    compare the aggregated nutritional information to a user nutritional profile to identify one or more nutritional opportunities; and select one or more food items from the plurality of food in a food datastore to provide the one or more nutritional opportunities by the following:
  (1) for each nutrient of each of the one or more food items designated for purchase, calculating a ratio by dividing a serving size of the designated food item for purchase by a serving size of a corresponding item in the plurality of food,
  (2) multiplying each calculated ratio of (1) by an amount of a respective nutrient in the plurality of food to obtain a first value of each nutrient for each one or more food items designated for purchase,
  (3) summing the first value of (2) for each nutrient to obtain a total value of each nutrient in the one or more food items designated for purchase,
  (4) respectively dividing the total value of (3) of each nutrient by a daily consumption amount for the nutrient to obtain a second value, the daily consumption amount being retrieved, by a processor, from a user datastore,
  (5) dividing the second value of (4) by a number of caloric days the one or more food items designated for purchase can supply,
  (6) obtaining a percent of daily consumption amount for each nutrient that is fulfilled by the one or more food items designated for purchase, and creating a sum based on the percent of daily consumption amount to obtain a nutrient deviation score,
  (7) selecting one or more food items from the plurality of food in the food datastore and adding the selected one or more food items to the one or more food items designated for purchase to create a hypothetical combination of food items designated for purchase, and repeating (1)-(6) to obtain a new deviation score of the nutrient deviation score, and
  (8) repeating (7) for a plurality of combinations of items in the plurality of food in the food datastore, and ranking obtained new deviation scores for each combination of items from the plurality of food in the food datastore with the one or more food items designated for purchase;
instructing a sponsor module to select one or more food items from the plurality of food in the food datastore provided by a sponsor;
instructing a seasonal model to receive weather data, and selecting one or more food items from the plurality of food in the food datastore based on the received weather data;
instructing an integration module to select one or more recommended food items based on aggregating the one or more food items selected by the nutrient optimization engine, the sponsor module, and the seasonal model;
assigning the one or more recommended food items to a recommendation; and
instructing a recommender module to send an indication of the recommendation for presentation via the GUI by instructing the GUI to include the recommendation, provided by the recommender module, in a second text box, wherein
  the processor, disposed in a user device, is configured to operate according to a computer readable medium having thereon computer-executable components that include the nutrient optimization engine, the sponsor module, the seasonal model, the integration module, and the recommender module;
  the food datastore includes records associated with the plurality of food, the records including nutritional information associated with each of the plurality of food;
  the user datastore includes records associated with nutritional guidelines according to parameters including at least two of age, sex, specialty diet, customized nutritional guideline, and activity level, wherein the user datastore includes the user nutritional profile associated with the user identifier and based on the designated parameters;
  a parameter interface, operated by the processor, is configured to receive the designated parameters associated with the user identifier;
  a purchase interface, operated by the processor, is configured to receive an indication of food designated for purchase; and
  the GUI, operated by the processor and disposed on the user device, includes:
    a first text box for one or more food items designated for purchase, and
    the second text box for one or more food items being recommended; and
    the input device being in the user device, the input device being operated by the processor, configured to receive an input associated with a food item via the GUI.

13. The method as claim 12 recites, further comprising aggregating nutritional information associated with a plurality of food items from a shopping cart, wherein the nutritional information compared includes the aggregated nutritional information.

14. The method as claim 12 recites, further comprising receiving registration of the user including authorization to store the designated parameters associated with the user including at least two of age, sex, specialty diet, and activity level and maintaining the user record according to the registration of the user.

15. The method as claim 12 recites, further comprising recommending
  adding an additional food item to a shopping cart to improve the nutritional opportunity relative to the nutritional guideline; or
  removing a food item from the shopping cart to improve the nutritional opportunity relative to the nutritional guideline.

16. The method as claim 12 recites, further comprising:
  maintaining the user record according to registration of the user;
  adding information to the user record associated with a purchase as previous purchase information; and
  basing the recommendation on previous purchase information from the user record.

17. A method of configuring a user device, the method comprising:
  creating a user record associated with a user identifier, wherein the user record includes a nutritional guideline determined based on designated parameters;
  receiving at least a first input and a second input associated, respectively, with a first food item and a second food item from an input device via a GUI,
  adding the first food item and the second food item to one or more food items designated for purchase;

selecting a record from records associated with a plurality of food corresponding to each of the one or more food items designated for purchase;
instructing a nutrient optimization engine to:
aggregate nutritional information in the selected record;
compare the aggregated nutritional information to a user nutritional profile to identify one or more nutritional opportunities; and
select one or more food items from the plurality of food in a food datastore to provide the one or more nutritional opportunities by the following:
(1) for each nutrient of each of the one or more food items designated for purchase, calculate a ratio by dividing a serving size of the designated food item for purchase by a serving size of a corresponding item in the plurality of food,
(2) multiply each calculated ratio of (1) by an amount of a respective nutrient in the plurality of food to obtain a first value of each nutrient for each one or more food items designated for purchase,
(3) sum the first value of (2) for each nutrient to obtain a total value of each nutrient in the one or more food items designated for purchase,
(4) respectively divide the total value of (3) of each nutrient by a daily consumption amount for the nutrient to obtain a second value, the daily consumption amount being retrieved, by a processor, from a user datastore,
(5) divide the second value of (4) by a number of caloric days the one or more food items designated for purchase can supply,
(6) obtain a percent of daily consumption amount for each nutrient that is fulfilled by the one or more food items designated for purchase, and create a sum based on the percent of daily consumption amount to obtain a nutrient deviation score,
(7) select one or more food items from the plurality of food in the food datastore and add the selected one or more food items to the one or more food items designated for purchase to create a hypothetical combination of food items designated for purchase, and repeat (1)-(6) to obtain a new deviation score of the nutrient deviation score,
(8) repeat (7) for a plurality of combinations of items in the plurality of food in the food datastore, and rank obtained new deviation scores for each combination of items from the plurality of food in the food datastore with the one or more food items designated for purchase;
instructing a sponsor module to select one or more food items from the plurality of food in the food datastore provided by a sponsor,
instructing a seasonal model to receive weather data, and selecting one or more food items from the plurality of food in the food datastore based on the received weather data,
instructing an integration module to select one or more recommended food items based on aggregating the one or more food items selected by the nutrient optimization engine, the sponsor module, and the seasonal model,
assigning the one or more recommended food items to a recommendation, and
instructing a recommender module to send an indication of the recommendation for presentation via the GUI by instructing the GUI to include the recommendation, provided by the recommender module, in a second text box, wherein
the user device is configured to operate according to a computer readable medium having thereon computer-executable instructions that include: the nutrient optimization engine, the sponsor module, the seasonal model, the integration module, and the recommender module;
the food datastore includes records associated with the plurality of food, the records including nutritional information associated with each of the plurality of food;
the user datastore includes records associated with nutritional guidelines according to parameters including at least two of age, sex, specialty diet, customized nutritional guideline, and activity level, wherein the user datastore includes the user nutritional profile associated with the user identifier and based on the designated parameters;
a parameter interface, operated by the processor, configured to receive the designated parameters associated with the user identifier;
a purchase interface, operated by the processor, is configured to receive an indication of food designated for purchase; and
the GUI, operated by the processor and disposed on the user device, the GUI including:
a first text box for one or more food items designated for purchase, and
the second text box for one or more food items being recommended; and
the input device being in the user device, the input device being operated by the processor, configured to receive an input associated with a food item via the GUI.

18. The method of configuring a device as claim 17 recites, further comprising receiving registration of the user including authorization to store the parameters associated with the user including at least two of age, sex, and activity level in the user record and to maintain the user record according to the authorization provided in the registration.

19. The method of configuring a device as claim 18 recites, further comprising receiving an indication of a food purchase, and adding information associated with the food purchase to the user record as previous purchase information.

20. The method of configuring a device as claim 19 recites, further comprising
receiving an indication to incorporate previous purchase information in recommendations including at least one item being a nutritionally complementary food, and wherein the nutritionally complementary food is based on the previous purchase information from the user record.

* * * * *